United States Patent [19]

Besse

[11] Patent Number: 5,846,564
[45] Date of Patent: Dec. 8, 1998

[54] EFFERVESCENT COMPOSITION CONTAINING IODINATED POLYVINYLPYRROLIDONE, AND USE THEREOF FOR DISINFECTION

[75] Inventor: Jérome Besse, Listrac-Medoc, France

[73] Assignee: Societe Civile Mission, Pauillac, France

[21] Appl. No.: 875,632

[22] PCT Filed: Jan. 30, 1996

[86] PCT No.: PCT/FR96/00157

§ 371 Date: Sep. 29, 1997

§ 102(e) Date: Sep. 29, 1997

[87] PCT Pub. No.: WO96/23510

PCT Pub. Date: Aug. 8, 1996

[30] Foreign Application Priority Data

Jan. 30, 1995 [FR] France ................................... 95 01047

[51] Int. Cl.⁶ ...................................................... A61K 9/46

[52] U.S. Cl. ........................ 424/466; 424/489; 514/772.3; 514/777

[58] Field of Search ..................................... 424/466, 464, 424/489

[56] References Cited

U.S. PATENT DOCUMENTS 5,089,606 2/1992 Cole et al. ................................ 536/54

Primary Examiner—Thurman K. Page
Assistant Examiner—James M. Spear
Attorney, Agent, or Firm—Jacobson, Price, Holman & Stern, PLLC

[57] ABSTRACT

Effervescent composition comprising in synergetic quantities: iodinated polyvinylpyrrolidone (IPVP) at least one effervescent agent, and at least one disintegrating agent. It may be presented in the form of powder, granules or tablets.

13 Claims, No Drawings

EFFERVESCENT COMPOSITION CONTAINING IODINATED POLYVINYLPYRROLIDONE, AND USE THEREOF FOR DISINFECTION

This application is a 371 of PCT/FR96/00157 filed Jan. 30, 1996.

This invention relates to an iodinated polyvinylpyrrolidone-based effervescent composition.

It relates to the use of this composition for the purposes of disinfection.

Iodine has long been used in various pharmaceutical forms (solution, tincture) in the fine disinfection of small wounds. Despite its efficacy, application of the product is limited due to the fact that it presents a certain number of side effects.

Iodinated polyvinylpyrrolidone (IPVP) is a complex of polyvinylpyrrolidone (PVP) and iodine. Owing to its complexation with the polyvinylpyrrolidone molecule, the iodine contained in the complex is released slowly and gradually.

IPVP is characterized by a wide range of applications, principally in the prophylactic field:

disinfection of hands, particularly in surgery,
antisepsis of the skin and mucosa, and in therapy:
use in cutaneous mycosis, pyodermitis and acne,
use in the treatment of vaginitis,
treatment of burns, decubitus and varicose ulcers.

This compound is a broad-spectrum antiseptic:

bactericidal on all bacteria, including chlamydiae and mycoplasms,
antifungal in relation to dermatophytes and candida,
antitrichomonas.

Iodinated polyvinylpyrrolidone (IPVP) is generally presented in the form of a solution.

There are, however, notable disadvantages with this formulation due to its poor conservation properties, high manufacturing price and storage and handling problems.

IPVP tablets have already been described but with specific reference to mucoadhesive and local use.

To the best of the applicant's knowledge, no IPVP preparation permitting the extemporaneous production of solutions, in the form of granules, tablets or any other solid form, has ever been described.

Owing to the particularly strong binding power of the PVPs, the IPVP tablets present in fact the major drawback of dissolving very slowly in aqueous media.

Thus, the abstracts of patent JP 63 225 308 (SANYO CHEMICAL CORPORATION Ltd.) describe compositions notably containing an iodine carrier which may be polyvinylpyrrolidone, an iodide or an iodine compound, an oxidizing agent, an acid or a base in powder form. The latter two compounds form an effervescent couple. This composition does not, however, comprise iodinated polyvinylpyrrolidone, a complex which has to be formed before it can be integrated in a composition. Moreover, the composition does not contain a disintegrating agent and consequently cannot be used for the extemporaneous production of IPVP solutions, but only for forming foam, as indicated in the abstracts hereabove mentioned.

Patent GB-A-2 108 386 (AUCHINCLOSS) describes compositions in dry forms containing an iodine source, such as a complex of polyvinylpyrrolidone and iodine, a non-reducing acid and a tensioactive agent capable of combining with iodine to form an iodophor. This patent makes no mention of the presence of a disintegrating agent nor even an effervescent couple.

Patent application PCT/GB 90 01 423 (AUCHINCLOSS) discloses a composition comprising an inorganic halide soluble in water, a strong oxidizing agent which will react with the halide so as to generate hypohalic ions, sulfamic acid, and a carbonate or bicarbonate soluble in water in order to produce, in reaction with the acid, an effervescent effect. The presence of a disintegrating agent is not mentioned in this application which preferentially concerns chlorine-based tablets.

U.S. Pat. No. 3,136,692 (STRONG CORB ARNER, INC.) concerns effervescent compositions containing polyvinylpyrrolidone, a solid organic acid and a therapeutic agent or a flavoring agent. Neither iodinated polyvinylpyrrolidone nor a disintegrating agent is mentioned in this patent.

It therefore emerges from an analysis of the current state of the art, and to the best of the applicant's knowledge, that none of the compositions described make it possible to obtain extemporaneously iodinated polyvinylpyrrolidone solutions.

It will also be noted that, with the compositions of the current state of the art, it is not possible to obtain reproducible solutions of IPVP presenting determined free iodine levels. This is particularly true in the case of the Japanese patent which associates free PVP and free iodine in foams, and which does not use a previously formed IPVP complex.

The applicant therefore endeavored to develop compositions which contain IPVP and which also permit extemporaneous, reproducible and easily applicable preparation of IPVP solutions.

He found that the association of IPVP, effervescent agents and disintegrating agents, in the form of granules or tablets, is preserved over a long period of time and rapidly gives an IPVP solution through the contact of this association with an aqueous medium.

This invention therefore relates to an effervescent composition for the extemporaneous preparation of IPVP solutions comprising in synergetic quantities:

iodinated polyvinylpyrrolidone (IPVP)
at least one effervescent agent, and
at least one disintegrating agent.

The compositions concerned by this invention possess the advantage of dissolving in at least ten minutes, and generally in three to five minutes, thus permitting an extemporaneous preparation of IPVP solution in contrast to the compositions described in the prior art which contain no disintegrating agent. These compositions also make it possible to obtain reproducible iodine levels in solution.

The expressions "effervescent agent" and "disintegrating agent" mean substances responding to the definitions given by Le Hir in "Abrégé de Pharmacie Galénique" (5th edition, published by Masson).

Such a composition advantageously comprises, by weight, 0.1% to 99%, preferentially 10% to 90% and even more preferentially 20% to 60% of IPVP in relation to the total weight of the composition.

Said effervescent agent is advantageously an association comprising citric acid and carbonic acid, or their derivatives. However, it may be any association of organic acid/carbonate substances giving effervescence. The citric acid derivatives which may be used in such a couple are, in particular, monosodium citrate or monohydrated or anhydrous citric acid.

A derivative of carbonic acid may be monosodium carbonate.

Citric acid and carbonic acid, or their derivatives, are advantageously contained in approximately identical quantities.

The disintegrating agent may be a substance presenting a structural similarity to IPVP; it possesses in particular a reticulated polyvinylpyrrolidone (PVP), or a reticulated carboxymethylcellulose. However, it may be any other substance or mixture of substances presenting a disintegrating effect such as defined above.

Advantageously, a composition according to this invention comprises, by weight, 40% to 60% of effervescent agent and 2% to 10%, preferentially 4% to 6%, of disintegrating agent.

Preferentially, the composition is presented in the form of a powder, granules or tablets.

Although this is not essential, the invention may also contain a buffer system with a pH close to 6, so as to limit the degradation of the IPVP. Such a buffer effect is advantageously provided through salts, such as $KH_2PO_4$ or by sodium hydroxide.

A water-repellent substance may also be contained in the composition in order to prevent moisture decomposition. Such a water-repellent substance may be, for example, colloidal silica.

The composition according to the invention may also contain one or more surfactants.

Advantageously, said composition is in the form of granules consisting of:

an internal phase comprising the IPVP and an effervescent couple, an external phase comprising a disintegrating agent and a lubricant.

This invention also relates to the use of a composition such as described above for the disinfection of skin and mucous membranes.

Once in solution, it may particularly be used in:

dermic, gynecological and foam solutions, or for mouth washes, impregnated compresses, wet pads, ointments.

These compositions have unquestionable practical as well as economic advantages as they facilitate the transportation and handling of IPVP.

They also have an industrial cost price which is far lower than the cost price of IPVP solutions. It is estimated that the difference between the two prices is at least 30%.

The tablets according to the invention may be obtained by a process in which the IPVP and the effervescent agent are mixed, and then the disintegrating agent and the other constituents of the tablets are introduced.

The tablet is then shaped using a compressing machine.

The entire process must be carried out in the absence of humidity.

Granules according to the invention may be obtained by a process similar to that used for tablets, the tablet compression stage being replaced by a compacting stage and then a granulation stage, for example using an ERWEKA AR 400 machine.

Granules with internal and external phases according to the invention may be obtained by a wet granulation process in which:

the internal phase is constituted by IPVP with, if required, a surfactant and an effervescent couple, the whole is wetted with water, the grain obtained is dried, and the external phase comprising the other constituents of the composition is added.

Those skilled in the art may refer to the general work entitled "Abrégé de Pharmacie Galénique" written by Le Hir and published by Masson, for the implementation of this invention and, in particular, for the preparation of the compositions covered by this invention.

This invention is illustrated by, without being limited to, the following examples:

EXAMPLE 1

Preparation of tablets according to the invention

Mixture (1) Introduce the IPVP and the effervescent agent in a TURBULA mixer or equivalent.

(2) Mix for 10 minutes at 50 rpm.

(3) Add the previously sifted colloidal silica and the disintegrating agent to the mixture obtained in step (2).

(4) Mix for 5 minutes at 50 rpm.

(5) Introduce the lubricant (PEG 6000 or equivalent) to the mixture obtained in step (4) and mix for 3 minutes.

(6) Store the mixture in a recipient away from humidity.

Compression (7) Fit the compressing machine with punches 20 mm in diameter.

(8) Carry out the compressing operation.

(9) Check the absolute humidity, weight and hardness of the tablets during production.

Optimal operating conditions

Humidity: 3 g of water per $m^3$ of dry air, i.e. 20% RH at 20° C.

The following tablets obtained by this process:

| GAL FORMULA 01-10 | Amount % (in weight) |
|---|---|
| IPVP (iodinated PVP) 30/06 | 46.70 |
| Anhydrous citric acid agent | 20.45 |
| Monosodium carbonate effervescent | 24.55 |
| Reticulated PVP (Polyplasdone XL) | 5 |
| Polyethylene glycol 6000 (PEG) (micronized) | 3 |
| Colloidal silica (Aerosil R 972) | 0.3 |
| Theoretical weight | 2.14g |

GAL FORMULA 01-08

In this formula, the anhydrous citric acid is replaced, at equivalent weight, by monohydrated citric acid.

These two formulas allow the tablet to dissolve totally in 5 minutes (GAL 01-10) and 6 minutes 30 seconds (GAL 01-08), respectively.

EXAMPLE 2

Preparation of granules according to the invention by wet method granulation

Wetting solution (1) Pour the surfactant into an appropriate recipient.

(2) Switch on the shaker fitted with a deflocculating device or equivalent. Speed: 50 rpm.

(3) Pour the amount of water required to yield the volume.

(4) Stop shaking as soon as the surfactant is entirely solubilized.

Wetting of IPVP (1) Introduce the IPVP in a planetary mixer fitted with an adjustment tube or equivalent.

(2) Move the mixer switch to speed 1.

(3) Pour the quantity of wetting solution, with or without the surfactant (weight/weight), then complete granulation with water until a satisfactory grain is obtained.

(4) Pour the grain obtained in step (3) in a thin layer on a heating plate.

(5) Dry the grain for a maximum of 7 hours at 60° C.

(6) Check loss through desiccation of the grain obtained in step (5) (less than 1%).

Granulation (7) Granulate the grain obtained in step (5) using an ERWEKA AR 400 granulating machine or equivalent on a grill 800 µm in diameter.

(8) Calibrate the grain obtained in step (7) on a 800 µm sieve.

Final mixture (9) Pour the mixture obtained in step (8) into a TUR-BULA type mixer or equivalent.

(10) Add the external phase excipients with the exception of the lubricant.

(11) Mix for 5 minutes at 50 rpm.

(12) Introduce the previously sifted lubricant to the mixture obtained in step 11 and mix for 3 minutes.

Compression

(13) Fit the compressing machine with punches 20 mm in diameter.

(14) Carry out the compressing operation.

(15) Check the absolute humidity, weight and hardness of the tablets during production.

Compression material

OA—Alternative type FROGERAIS.

This process gives the following granules whose compositions are listed in Table I below.

These granules dissolve the tablet respectively in 7 minutes (GAL 02-11 and GAL 02-13), less than 5 minutes (GAL 02-14), and 3 minutes 30 seconds (GAL 02-15 and GAL 02-16).

In this process, nonoxymol may be replaced by Cremophor, Tween 80 or any other equivalent surfactant.

In order to facilitate the flow during the formation of the outer layer, lactose may be added to the compounds of this layer.

EXAMPLE 3

Influence of the presence of a disintegrating agent.

Two types of compositions, one containing a disintegrating agent, reticulated PVP (polyplasdone XL), and the other without this agent, respectively called GAL 01.16 and GAL 01.17, were produced by direct compression as described in Example 1.

The effervescence times of 20 mm tablets in 10 ml of water were then tested.

Table II shows that the GAL 01.16 tablets dissolve in approximately 4 minutes, whereas the tablets without disintegrating agent GAL 01.17 have still not dissolved after 24 hours.

This provides clear proof of the need for the disintegrating agent and demonstrates the resulting effect.

TABLE 1

Composition of granules obtained according to Example 2

| Weight % | GAL 02.11 | GAL 02.13 | GAL 02.14 | GAL 02.15 | GAL 02.16 |
|---|---|---|---|---|---|
| Inner layer | | | | | |
| IPVP 30/06 | 46.7 | 41.3 | 21.6 | 35.05 | 30.28 |
| Surfactant (20% Nonoxynol solution) | | 0.94 | 0.49 | 0.7 | 0.6 |
| KH$_2$PO$_4$ 0.2 N solution) | | | | 0.8 | 0.69 |
| NaOH (0.2 N solution) | | | | 0.147 | 0.127 |
| Monosodium carbonate | 24.53 | | | | |
| Anhydrous citric acid | 20.45 | | | | |
| Micronized PEG 6000 | 3 | | | | |
| Outer layer | | | | | |
| Micronized PEG 6000 | | 2.97 | 2.99 | 3 | 3 |
| Monosodium citrate | | 27.75 | 39.02 | 30.81 | 33.61 |
| Monosodium carbonate | | 21.78 | 30.63 | 24.19 | 26.39 |
| Reticulated PVP (Polyplasdone XL) | 5.02 | 4.96 | 4.97 | 5 | 5 |
| Colloidal silica (Aerosil R972) | 0.3 | 0.3 | 0.29 | 0.3 | 0.3 |
| Amount of IPVP per tablet | 1 g | 1 g | 500 mg | 750 mg | 650 mg |

TABLE 1-continued

Composition of granules obtained according to Example 2

| Weight % | FORMULATIONS | | | | |
|---|---|---|---|---|---|
| | GAL 02.11 | GAL 02.13 | GAL 02.14 | GAL 02.15 | GAL 02.16 |
| Theoretical weight (20 mm tablet) | 2.14 g | 2.4 g | 2.3 g | 2.14 g | 2.14 g |

TABLE II

| | GAL 01.16 | GAL 01.17 |
|---|---|---|
| IPVP 30/06 | 36.7 | 38.6 |
| Monosodium citrate | 30.81 | 33.5 |
| Monosodium carbonate | 24.19 | 26.31 |
| Polyplasdone XL | 5 | — |
| Aerosil R 972 | 0.3 | 0.33 |
| Sodium benzoate | 3 | 3.26 |
| IPVP amount of per tablet | 750 mg | 750 mg |
| Theoretical weight of tablets (20 mm) | 2.044 g | 2.049 g |
| Disintegration time (10 ml) | 4 min | >24 hours |

I claim:

1. An effervescent composition for the extemporaneous preparation of IPVP solutions comprising in synergetic quantities:
   iodinated polyvinylpyrrolidone (IPVP)
   at least one effervescent agent, and
   at least one disintegrating agent.

2. A composition according to claim 1, which comprises, by weight, 0.1% to 99%, of IPVP in relation to the total weight of the composition.

3. A composition according to claim 1, wherein the effervescent agent is an association comprising on one hand citric acid and on the other carbonic acid, or their derivatives.

4. A composition according to claim 3, which contains approximately the same molar quantities of citric and carbonic acids, or their derivatives.

5. A composition according to claim 1, wherein the disintegrating agent is a reticulated polyvinylpyrrolidone.

6. A composition according to claim 1, wherein the disintegrating agent is a reticulated carboxymethylcellulose.

7. A composition according to claim 1, which it contains a buffer system with a pH close to 6.

8. A composition according to claim 7, wherein the buffer system comprises $KH_2PO_4$ and NaOH.

9. A composition according to claim 1, which contains a water-repellent substance.

10. A composition according to claim 1, which is in the form of powder, granules or tablets.

11. A method for disinfecting skin or mucosa which comprises dissolving a composition of claim 1 in water and applying an effective amount of the resulting solution to the skin or mucous membrane.

12. A composition according to claim 2 which comprises, by weight, from 10% to 90% of IPVP in relation to the total weight of the composition.

13. A composition according to claim 12 which comprises, by weight, from 20% to 60% of IPVP in relation to the total weight of the composition.

* * * * *